US010743993B2

(12) United States Patent
Ryan (10) Patent No.: US 10,743,993 B2
(45) Date of Patent: Aug. 18, 2020

(54) PROSTHETIC VALVE SIZER AND ASSEMBLY INCLUDING SAME

(71) Applicant: Medtronic, Inc., Minneapolis, MN (US)

(72) Inventor: Timothy Ryan, Minnetrista, MN (US)

(73) Assignee: Medtronic Inc., Minneapolis, MN (US)

( * ) Notice: Subject to any disclaimer, the term of this patent is extended or adjusted under 35 U.S.C. 154(b) by 1101 days.

(21) Appl. No.: 15/001,777

(22) Filed: Jan. 20, 2016

(65) Prior Publication Data

US 2016/0206428 A1    Jul. 21, 2016

Related U.S. Application Data

(60) Provisional application No. 62/105,864, filed on Jan. 21, 2015.

(51) Int. Cl.
*A61F 2/24* (2006.01)

(52) U.S. Cl.
CPC .... *A61F 2/2496* (2013.01); *A61F 2250/0018* (2013.01); *A61F 2250/0029* (2013.01)

(58) Field of Classification Search
CPC ............ A61F 2/2496; A61F 2250/0018; A61F 2250/0029; A61F 2250/0014
See application file for complete search history.

(56) References Cited

U.S. PATENT DOCUMENTS

| | | | |
|---|---|---|---|
| 4,106,129 A | 8/1978 | Carpentier et al. | |
| 4,851,000 A * | 7/1989 | Gupta | A61F 2/2418 623/2.18 |
| 5,037,434 A | 8/1991 | Lane | |
| 6,350,281 B1 | 2/2002 | Rhee | |
| 6,562,069 B2 * | 5/2003 | Cai | A61F 2/2412 623/2.12 |
| 7,258,698 B2 | 8/2007 | Lemmon | |
| 2005/0085904 A1 * | 4/2005 | Lemmon | A61F 2/2427 623/2.11 |
| 2010/0022948 A1 * | 1/2010 | Wilson | A61F 2/2466 604/95.04 |

* cited by examiner

*Primary Examiner* — Devin B Henson (57) ABSTRACT

Various embodiments of a prosthetic valve sizer and a method that utilizes such valve sizer are disclosed. In one or more embodiments, the prosthetic valve sizer can include a sizer body including an annular base and a post extending from the annular base. The prosthetic valve sizer can also include a resilient tip extending from the post of the sizer body. The resilient tip can include a material different from and more flexible than a material of the sizer body.

11 Claims, 8 Drawing Sheets

PROSTHETIC VALVE SIZER AND ASSEMBLY INCLUDING SAME

CROSS-REFERENCE TO RELATED APPLICATION

This application claims priority to U.S. Provisional Patent Application Ser. No. 62/105,864 filed Jan. 21, 2015, which is incorporated herein by reference.

BACKGROUND

Various types and configurations of prosthetic heart valves, used to replace diseased natural human heart valves, are known in the art. The actual shape and configuration of any particular prosthetic heart valve is, of course, dependent to some extent upon the valve being replaced (i.e., mitral valve, tricuspid valve, aortic valve, and pulmonary valve). In general terms, however, the prosthetic heart valve design attempts to replicate the function of the valve being replaced and thus will include valve leaflet like structures. With this in mind, prosthetic heart valves including valve leaflets are generally categorized as either forming relatively flexible leaflets or relatively rigid leaflets.

The category including prosthetic heart valves which form relatively flexible leaflets includes bioprosthetic heart valves having leaflets made of a biological material as well as prosthetic heart valves having leaflets made of synthetic (e.g., polymeric) material. Flexible leaflet prosthetic heart valves are generally categorized as having a frame or stent or as having no stent. The stent in a stented prosthetic heart valve normally includes a substantially circular base or stent ring around which an annular suture material is disposed for suturing the prosthesis to heart tissue. The stent ring including the annular suture material is typically referred to as a sewing ring. Further, the stent forms at least two, typically three, support structures extending from a stent ring. The support structures are commonly referred to as stent posts or commissure posts and can include an internal, rigid yet flexible structure extending from the stent ring, covered by a cloth-like material similar to that of the annular suture material. The stent or commissure posts define the junction between adjacent tissue or synthetic leaflets otherwise secured thereto.

Examples of prosthetic heart valves are described in U.S. Pat. No. 4,106,129 to Carpentier et al. and U.S. Pat. No. 5,037,434 to Lane. These disclosures detail a conventional configuration of three leaflets where one leaflet is disposed between each pair of stent or commissure posts. The Hancock™ II Bioprosthesis, manufactured by Medtronic, Inc., Minneapolis, Minn., is a commercially available example of a bioprosthetic valve. The Hancock™ II is available in various sizes such that it may be implanted in patients having corresponding varying sizes of heart valve annuli.

During valve replacement surgery, the heart valve prosthesis is implanted within the patient's heart using either a supra-annular or intra-annular implant technique. The supra-annular implant technique sutures the prosthetic heart valve above the annulus corresponding to the heart valve to be replaced. The intra-annular implant technique sutures the prosthetic heart valve within the annulus corresponding to the heart valve to be replaced.

Ideally, the heart valve annulus is formed of relatively healthy tissue receptive to some shaping by the surgeon in preparation of receiving the heart valve prosthesis; however, due in part to the space and time constraints during valve replacement surgery, the shape of the resulting annulus is often less than perfect for the attachment of a heart valve prosthesis. At times, the annulus and/or the patient's natural leaflets are calcified, requiring complete annular debridement or removal of the hardened tissue. The annular debridement results in a less defined annulus ledge and larger overall orifice into which, or above which, the prosthetic heart valve is to be attached. As such, the size and contour of each annulus varies widely from patient to patient.

Due to the uneven nature of the annuli, a surgeon needs to select a properly sized prosthetic heart valve to match a particular patient's annulus. Typical annulus sizers are simple cylinders made out of rigid plastics, where the cylinder diameter corresponds to a size of a particular prosthetic heart valve. During surgery, a surgeon typically has a number of sizers at his disposal, each sizer having a different size or diameter (i.e., each sizer relating to a different size of prosthetic heart valve). A surgeon inserts the sizer or a series of different sizers into the valve opening to measure the size of the valve opening. Upon determining the size of the valve opening, the surgeon selects a heart valve prosthesis for implantation having a size believed to correspond to the size of the valve opening. Since the properties of the materials from which current sizers are constructed are often rigid and do not match the properties of actual prosthetic heart valves, it can be difficult to select the appropriate size heart valve for the patient when utilizing such sizers.

SUMMARY

In general, the present disclosure provides various embodiments of a prosthetic heart valve sizer and an assembly that includes the valve sizer. In one or more embodiments, the prosthetic heart valve sizer includes a resilient tip attached to a post of a sizer body.

In one aspect, the present disclosure provides a prosthetic valve sizer that includes a sizer body. The sizer body includes an annular base and a post extending from the annular base. The prosthetic valve sizer also includes a resilient tip extending from the post of the sizer body. The resilient tip includes a material different from and more flexible than a material of the sizer body.

In another aspect, the present disclosure provides a valve sizer assembly that includes a handle including a first end and a second end. The assembly also includes a prosthetic valve sizer connected to the first end of the handle. The prosthetic valve sizer includes a sizer body including an annular base and a post extending from the base, and a resilient tip extending from the post of the sizer body. The resilient tip includes a material different from and more flexible than a material of the sizer body.

In another aspect, the present disclosure provides a method for evaluating a heart valve annulus to determine a proper size of a prosthetic heart valve to be sewn to the valve annulus during heart valve replacement surgery. The method includes providing a prosthetic valve sizer. The prosthetic valve sizer includes a sizer body including an annular base and a post extending from the base, and a resilient tip extending from the post of the sizer body. The resilient tip includes a material different from and more flexible than a material of the sizer body. The method further includes inserting the valve sizer into an opening of the heart valve annulus to determine whether the valve sizer properly fits and conforms with the heart valve annulus; and selecting the prosthetic heart valve to be sewn to the heart valve annulus based upon the determination of whether the valve sizer properly fit and conformed to the heart valve annulus.

In another aspect, the present disclosure provides a prosthetic valve sizer that includes a sizer body including an annular base and a post extending from the base. The prosthetic valve sizer also includes a resilient ring extending from the sizer body adjacent the annular base of the sizer body. The resilient ring includes a material different from and more flexible than a material of the sizer body. The resilient ring further includes a protrusion formed on an outer surface of the resilient ring.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of and" comprises at least one of followed by a list refers to any one of the items in the list and any combination of two or more items in the list.

The phrases "at least one of and" comprises at least one of followed by a list refers to any one of the items in the list and any combination of two or more items in the list.

As used herein, the term "or" is generally employed in its usual sense including "and/or" unless the content clearly dictates otherwise. The use of the term "and/or" in certain portions of this disclosure is not intended to mean that the use of "or" in other portions cannot mean "and/or."

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

In general, the present disclosure provides various embodiments of a prosthetic heart valve sizer and an assembly that includes the valve sizer. In one or more embodiments, the prosthetic heart valve sizer includes a tip that extends from a post of a sizer body. The tip can, in one or more embodiments, be a resilient tip. Further, in one or more embodiments, the valve sizer can also include a ring that extends from the sizer body adjacent an annular base of the sizer body. In one or more embodiments, the ring of the sizer can be a resilient ring.

Sizing of prosthetic heart valves can be an important element of a successful clinical procedure. In one or more embodiments, a prosthetic heart valve sizer can be utilized to replicate the prosthetic heart valve and to facilitate measurement and/or evaluation of critical parameters or anatomical features. In addition, the physical configuration of the sizer can facilitate accurate, reproducible, and atraumatic assessment of fit of the appropriate sized heart valve in the patient anatomy prior to formally selecting the heart valve. Since most prosthetic heart valves are sutured into the patient anatomy with a fabric sewing ring or cuff, the physical properties of the heart valve sizer sewing ring can, in one or more embodiments, match that of the replacement heart valve.

Figure 1:
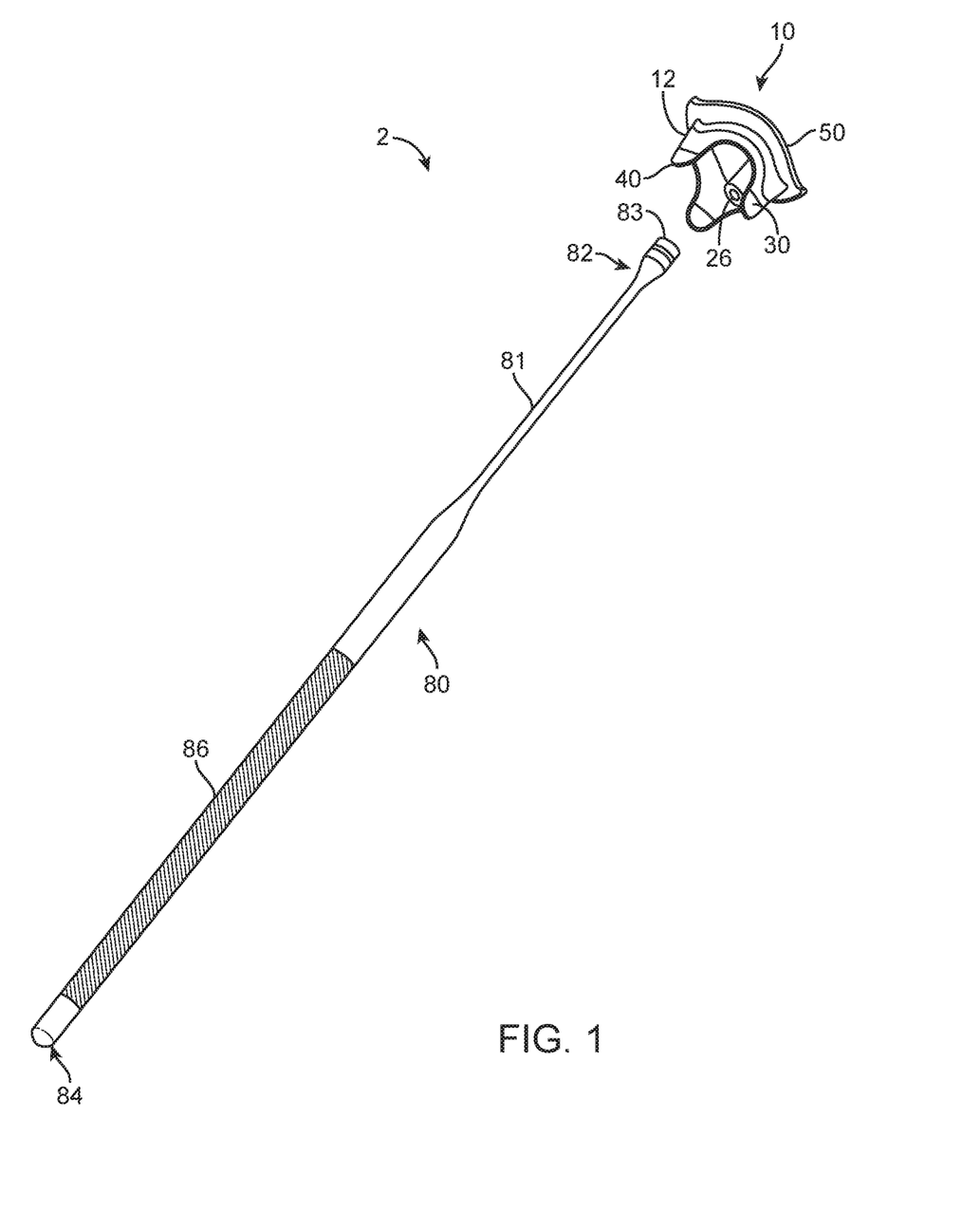
FIG. 1 is a schematic perspective view of one embodiment of a prosthetic valve sizer assembly.

FIG. 1 is a schematic perspective view of one embodiment of a valve sizer assembly 2. The assembly 2 includes a handle 80 including a first end 82 and a second end 84. Connected to the handle 80 is a prosthetic valve sizer 10. The handle 80 also includes a connector 83 on the first end 82 to interface with and facilitate coupling of the sizer 10 with the handle. In one or more embodiments, the connector 83 is formed to facilitate a snap connection, a threaded connection, or any other spatially feasible and biocompatible, selective or permanent attachment to the sizer 10. In one or more embodiments, the handle 80 is integral with the sizer 10, i.e., the handle and sizer are manufactured together at the same time; that is, being made together as one part and not two separately manufactured parts that are subsequently joined together.

The handle 80 can include any suitable material or combination of materials. In one or more embodiments, a shaft 81 of the handle 80 is formed of a bendable, biocompatible metal including but not limited to stainless steel or nitinol. Further, the handle 80 can include a grip portion 86 near the second end 84 thereof to aid a surgeon in grasping and manipulating the handle. The grip portion 86 can have a larger dimension or diameter than the shaft 81 to facilitate ergonomic handling of the handle 80 by the surgeon. The grip portion 86 can be formed of a polymeric material to facilitate gripping of the handle 80. Alternatively, other constructions are equally acceptable, and the grip portion 86 can be eliminated entirely.

The assembly 2 can include any suitable prosthetic valve sizer 10. The prosthetic valve sizer 10 includes a sizer body 12 including an annular base (not shown) and one or more posts 30 extending from the base. The sizer 10 also includes tips 40 extending from the posts 30 and a ring 50 extending from the sizer body 12 adjacent the annular base as is further described herein.

Figure 2:
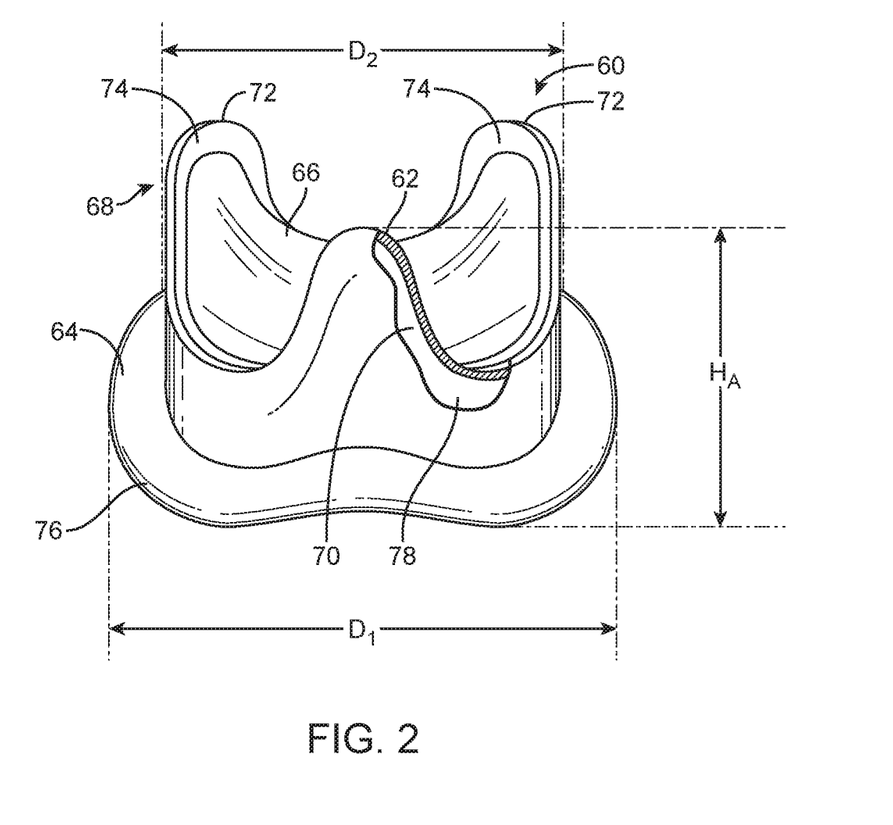
FIG. 2 is a schematic perspective view of a prosthetic heart valve.

In general, the sizer 10 is representative of a prosthetic heart valve, such as prosthetic heart valve 60 illustrated in FIG. 2. In one or more embodiments, the prosthetic heart valve 60 includes a stent 62, a sewing ring 64, and leaflets 66. As is known in the art, the stent 62 can provide a support framework for the prosthetic heart valve 60. The stent 62 can include an inner frame member or stent ring 78, which typically defines a circular or parabolic ring, and stent posts 70.

Each of the stent posts 70 extends from the stent ring 78 and terminates in a rounded tip or free end 72 opposite the stent ring 78. As is known in the art, the internal structure of each of the stent posts 70 is formed as a stiff but resiliently bendable material. This construction allows the stent posts 70 to be inwardly deflected from the orientation illustrated in FIG. 2 by an external force, such as an external force from an insertion handle used to position the prosthetic heart valve 60, during use. Once this external force is removed, however, the stent posts 70 return to the original position illustrated in FIG. 2. Further, a cloth cover 74 can be formed over the stent ring 78 and the stent posts 70. The cover 74 can be formed of a biocompatible, fabric material. In general, the stent 62 and the cover 74 form an annular extension 68.

The sewing ring 64 is coupled to and extends around the stent ring 78 opposite the stent posts 70. The sewing ring 64 serves as a flexible flange for subsequent suturing of the prosthetic heart valve 60 to a heart valve annulus. The sewing ring 64 can include a cloth cover 76, similar to the cloth cover 74, to facilitate suturing of the sewing ring to the stent 64 and the heart valve annulus.

Each of the leaflets 66 is sutured to the cloth cover 74. In particular, the leaflets 66 are sutured to the cloth cover 74 that covers the stent posts 70 such that each leaflet extends between two of the stent posts 70. Each of the leaflets 66 is also sutured to the cloth cover 76 covering the stent ring 64 between the two stent posts 70. The leaflets 66 can be made of biological or synthetic (e.g., polymeric) material and are configured to open and close to regulate blood flow when implanted.

In one or more embodiments, the annular extension 68 can have a first flexibility and the sewing ring 64 can have a second flexibility. The first flexibility normally differs from the second flexibility. As such, the entire prosthetic heart valve 60 accordingly defines a variable flexibility. Further, it will be understood that the described prosthetic heart valve 60 is but one acceptable configuration, e.g., more or less than three of the stent posts 70 can be provided, the stent posts may incorporate a different covering 74, and/or the covering may be eliminated.

The prosthetic heart valve 60 is available in various sizes corresponding to the various sizes of annuli found in heart valve replacement patients. In one or more embodiments, the prosthetic heart valve 60 can have a sewing ring maximum diameter $D_1$ of about 18 mm to 30 mm. Further, in one or more embodiments, the prosthetic heart valve 60 can also have a maximum stent diameter $D_2$ that is less than the sewing ring maximum diameter $D_1$ and that ranges in sizes accordingly. An overall or maximum height $H_A$ can also vary with differently sized prosthetic heart valves 60.

Figure 3:
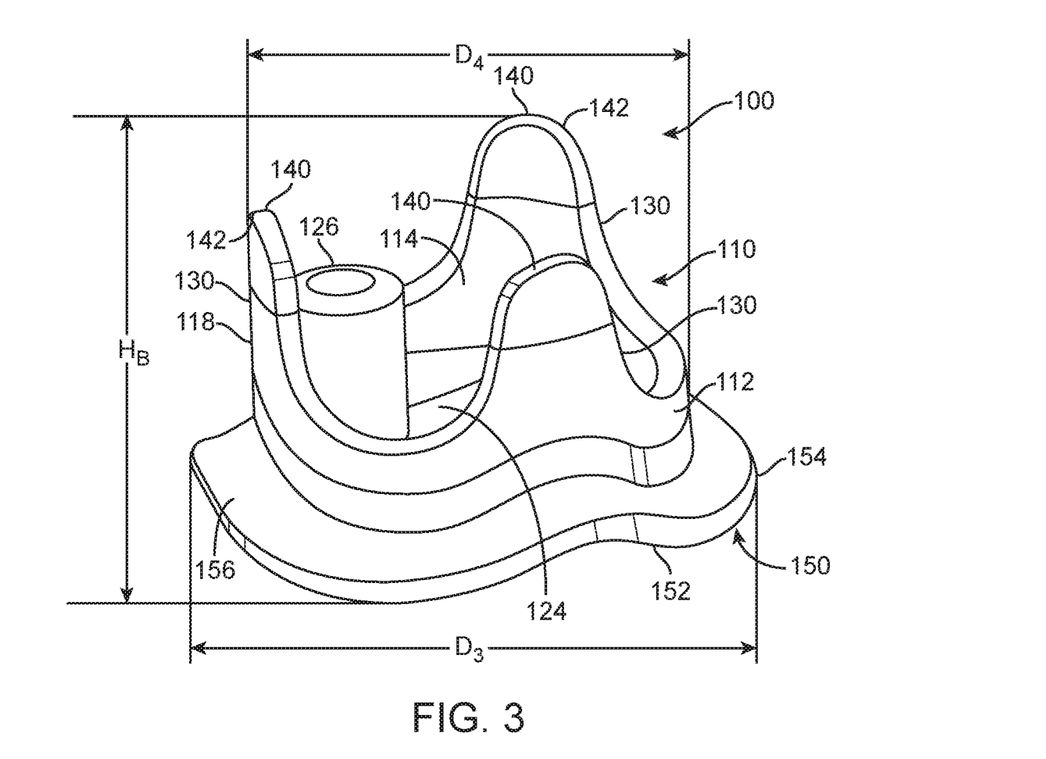
FIG. 3 is a schematic perspective view of one embodiment of a prosthetic valve sizer.
Figure 4:
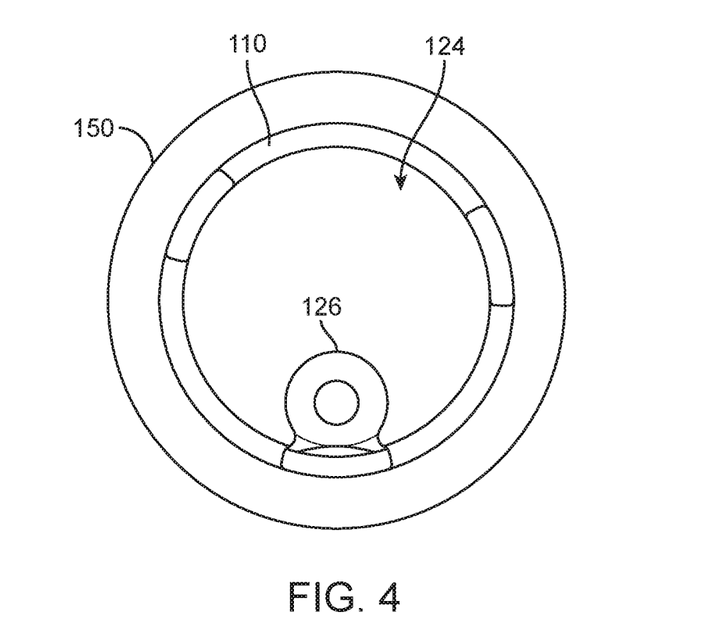
FIG. 4 is a schematic top view of the prosthetic valve sizer of FIG. 3.
Figure 5:
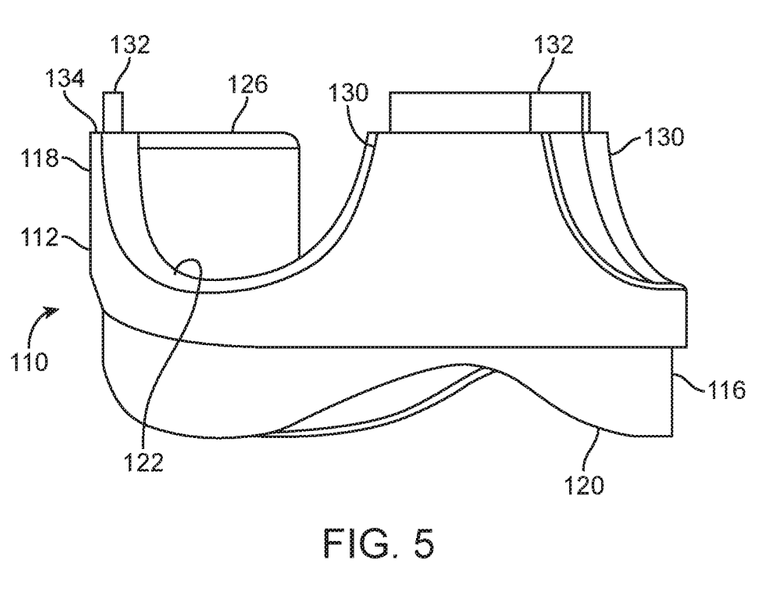
FIG. 5 is a schematic perspective view of a sizer body of the prosthetic valve sizer of FIG. 3.

As mentioned herein, the assembly 10 of FIG. 1 can include any suitable prosthetic valve sizer 10 that can be representative of any suitable prosthetic heart valve. For example, FIGS. 3-5 are various views of one embodiment of a prosthetic valve sizer 100. The sizer 100 includes a sizer body 110. The sizer body 110 includes an annular base 120 (FIG. 5) and one or more posts 130 that extend from the base. The sizer 100 also includes one or more tips 140, each of which extending from a post 130 of the sizer body 110. The tips 140 can, in one or more embodiments, be resilient tips as is further described herein.

In one or more embodiments, the sizer 100 can also include a ring 150 that extends from the sizer body 110 adjacent the annular base 120 of the sizer body. As used herein, the phrase "adjacent the annular base" means that an element is disposed closer to the annular base of the sizer body then to the posts of the sizer body. The ring 150 can, in one or more embodiments, be a resilient ring as is further described herein. Further, in one or more embodiments, the sizer 100 also includes a receiver 126 configured to receive a first end of a handle, e.g., first end 82 of handle 80 of FIG. 1.

The sizer body 110 includes an outer surface 112 and an inner surface 114. The sizer body 110 can also include an opening 124 defined by the inner surface 114. In one or more embodiments, the sizer body 110 can be a solid body that does not include opening 124. Further, the sizer body 110 can take any suitable shape or combination of shapes. In one or more embodiments, the sizer body 110 is sized and shaped in a manner similar to the stent 62 of the prosthetic heart valve 60. The sizer body 110 can represent the heart valve stent 62. The sizer body 110 can include any suitable number of posts 130. As illustrated in FIGS. 3-5, the sizer body 110 includes three posts 130 that extend from the annular base 120. Alternatively, the sizer body 110 can include two posts to resemble a two stent post-type prosthetic heart valve (not shown). Each of the posts 130 are sized and spaced from one another representative of how the stent posts 70 are sized and spaced from one another. Accordingly, the sizer 100 can include an overall height $H_B$ that is substantially equal to the overall height $H_A$ of the prosthetic heart valve 60. Further, the sizer body 110 can define a maximum diameter $D_4$ substantially equal to the maximum stent diameter $D_2$. In one or more embodiments, the height $H_B$ of the sizer 100 is within 1 mm of the height $H_A$, and the maximum diameter $D_4$ of the sizer is within 1 mm of the maximum stent diameter $D_2$.

The sizer body 110 can include any suitable flexibility value or values. In one or more embodiments, the sizer body 110 includes a flexibility representative of or approximating the actual flexibility of the annular extension 68 of the heart valve 60, i.e., the sizer body 110 has a flexibility similar to the flexibility of the annular extension. As such, the sizer body 110 can be formed to be stiff but resiliently bendable.

In one or more embodiments, the sizer body 110 can be formed of at least one elastomeric material including, but not limited to, Santoprene, silicone, polyurethane, polyester fabric, and combinations thereof. The sizer body 110 achieves a representative flexibility in a similar manner as described with respect to the resilient ring 150. The representative flexibility of sizer body 110 can be achieved by varying the material thickness, by increasing the durometer of the material, and/or by placing a stiffening element within an over-molded elastomeric material. In one or more embodiments, the sizer body 110 has a flexibility within 5% to 10% of the flexibility of the annular extension 68 of the stent 62. In one or more embodiments, the sizer body 110 has a flexibility in the range of 90 to 110% of the annular extension 68 of the heart valve 60.

Because the ring 150 and the sizer body 110 each have a size and shape approximating the size and the shape of the sewing ring 64 and the stent 62, respectively, the overall size and shape of the sizer 100 approximates the size and shape of the prosthetic heart valve 60. Similarly, since the sizer body 110 and the ring 150 can, in one or more embodiments, have different flexibilities representative of the first flexibility of the stent 62 and the second flexibility of the sewing ring 64, respectively, i.e., the overall sizer 100 can define a variable flexibility. With this in mind, the variable flexibility of the sizer 100 can be representative of or substantially equal to the variable flexibility of the prosthetic heart valve 60.

Notably, although the sizer 100 can be representative of the prosthetic heart valve 60, it is not necessary for the sizer to include the leaflets 66 as illustrated in FIGS. 3-5; however, in one or more embodiments, the sizer 100 can include representations of the leaflets 66. The sizer 100 can be sterilizable for reuse. In particular, the sizer 100 can be formed such that the outer surfaces of the sizer are substantially continuous to promote the proper sterilization of the sizer between uses. To facilitate reuse, the sizer 100 can be produced from materials that simulate the properties of the cloth covers 74 and 76 (FIG. 2) described herein with respect to prosthetic heart valve 60.

In one or more embodiments, the sizer body 110 can include a receiving surface 116 formed on the outer surface 112 of the sizer body as shown in FIG. 5. The receiving surface 116 can include an outer circumference that is less than an outer circumference of the outer surface 112 of the sizer body 110 such that the sizer body can receive the resilient ring 150. The receiving surface 116 can be adapted such that the resilient ring 150 is flush with the outer surface 112 of the sizer body 110. The sizer body 110 can also include tabs 132 extending from a receiving surface 134 on one or more of the posts 130 of the sizer body. The tabs 132 can be formed such that they can receive tips 140 as is further described herein. Further, in one or more embodiments, the sizer body 110 can include an upper surface 122 that extends between posts 130. In one or more embodiments, the upper surface 122 can take an arcuate shape similar to the shape of the stent 62 of heart valve 60.

As mentioned herein, the sizer 100 can include one or more tips 140 that extend from one or more posts 130 of the sizer body 110. The tips 140 can take any suitable shape or combination of shapes. In one or more embodiments, the tips 140 can include a curved upper surface 142 similar to the curved upper surface 72 of stent posts 70 of valve 60.

In one or more embodiments, the tips 140 can include any suitable material or combination of materials, e.g., an elastomeric material such as Santoprene, silicone, polyurethane, and combinations thereof. In one or more embodiments, the tips 140 can a include material or combination of materials that provide the tips with any suitable degree of resiliency and flexibility. As used herein, the term "resilient" means that the particular element is able to recoil or spring back into shape after bending, stretching, or being compressed. In one or more embodiments, the tips 140 can also be flexible. The tips 140 can include any suitable amount of flexibility. The representative flexibility of the tips 140 can be achieved using any suitable technique or combination of techniques, e.g., by varying material thickness of the tips, by varying a durometer of the material of the tips, or by forming the tips to include a stiffening element within an over-molded elastomeric material.

In one or more embodiments, the tips 140 can include a material that is different from a material of the sizer body 110. In one or more embodiments, the tips 140 can include a material that is more flexible than the material of the sizer body 110. In one or more embodiments, the tips 140 and the sizer body 110 can include the same material or materials.

The tips 140 can be disposed on posts 130 of the sizer body 110 using any suitable technique or combination of techniques. In one or more embodiments, the tips 140 can be disposed on the posts 130 of the sizer body 110 by attaching the tips to the posts. For example, each tip 140 can include a hollow interior portion that is configured to receive tab 132 of the post 130. The tips 140 can then be adhered to the tabs 132 and/or receiving surfaces 134 of the post 130 using any suitable adhesive. Alternatively, the tips 140 can include a heat shrinkable material such that the tips can be positioned over tabs 132 and then heated such that they become attached to the tabs and/or the receiving surfaces 134 of the posts. In one or more embodiments, the tips 140 can be molded onto posts 130 as is further described herein.

The sizer 100 also includes ring 150. The ring 150 can take any suitable shape or combination of shapes. In one or more embodiments, the ring 150 is sized and shaped in a similar manner as the sewing ring 64 of the prosthetic heart valve 60. Accordingly, the ring 150 can have a circular or parabolic shape and contour substantially similar to or matching the shape and contour of the sewing ring 64, such that each exposed dimension of the ring 150 is within, e.g., 1 mm of the corresponding exposed dimension of the sewing ring. In one or more embodiments, the ring 150 can define a maximum diameter $D_3$ substantially equal to the maximum sewing ring diameter $D_1$ of the prosthetic heart valve 60. Otherwise stated, the maximum diameter $D_3$ of the ring 150 is within 1 mm of the maximum sewing ring diameter $D_1$. Furthermore, the ring 150 can be formed with a flexibility representative of or approximating the flexibility of the sewing ring 64. Notably, a representative flexibility is a flexibility in which the ring 150 deforms or conforms to an area in a substantially similar manner under substantially similar external forces as the sewing ring 64 being represented. In other words, the ring 150 can have a substantially similar flexibility as the sewing ring 64. In one or more embodiments, the ring 150 can have a flexibility within 5% to 10% of the flexibility of the sewing ring 64. In one or more embodiments, the ring 150 can have a flexibility in the range of 90 to 110% of the sewing ring 64. The representative flexibility of the ring 150 can be achieved using any suitable technique or combination of techniques, e.g., by varying material thickness of the ring 150, by varying a durometer of the material from the ring, or by forming the ring to include a stiffening element within an over-molded elastomeric material.

The ring 150 can include any suitable material or combination materials, e.g., the same materials as those described for the tips 140. Further, the ring 150 can be a resilient ring. In one or more embodiments, the ring 150 can also be flexible. The ring 150 can include any suitable values of flexibility.

In one or more embodiments, a material of the ring 150 can be the same as the material of the sizer body 110. Alternatively, in one or more embodiments, the material of the ring 150 can be different from the material of the sizer body 110. Further, in one or more embodiments, the material of the ring 150 can be the same as the material of the tips 140. In one or more embodiments, the material of the ring 150 can be different from the material of the tips 140.

The sizer 100 can also include receiver 126 configured to receive a first end of a handle, e.g., first end 82 of handle 80 of FIG. 1. The receiver 126 can be sized and shaped to receive a connector (e.g., connector 83 of handle 80) of the first end of the handle via a snap connection, a threaded connection, or any other biocompatible, selective or permanent coupling technique. As illustrated in FIG. 4, the receiver 126 is disposed on the inner surface 114 of the sizer body 110. The receiver 126 can be attached to the inner surface 114 of the sizer body 110 using any suitable technique or combination of techniques. In one or more embodiments, the receiver 126 is integral with the receiver body 110. In one or more embodiments, the receiver 126 can be substantially centered with respect to the ring 150 and the sizer body 110 as described, e.g., in U.S. Pat. No. 7,258,698 to Lemmon.

With additional reference to FIG. 1, assembling the sizer assembly 2 can include mating the connector 83 of the handle 80 with the receiver 126 of the sizer 100. Although illustrated as a snap connection, in other embodiments the handle 80 is coupled with the sizer 100 in one of a plurality of fashions including a threaded attachment or any other spatially feasible, biocompatible attachment. In one or more embodiments, the handle 80 is selectively coupled with the sizer 100 such that the handle 30 can be selectively removed from the sizer and selectively coupled with other representative sizers (not illustrated). In one or more embodiments, the handle 80 is permanently coupled to the sizer 100.

In one or more embodiments, the sizer 100 can be utilized without a handle. For example, in one or more embodiments, the sizer 100 can include a protrusion disposed adjacent to or in place of receiver 126 such that a clinician can utilize forceps or other device to grasp the sizer.

In one or more embodiments, the sizer 100 can include indicia 118 disposed on any suitable portion of the sizer. For example, in the embodiment illustrated in FIGS. 3-5, indicia 118 are disposed on the outer surface 112 of the sizer body 110. Indicia 118 can also be disposed on the ring 150, the tips 140, or the interior surface 114 of the sizer body. The indicia 118 can be formed using any suitable technique or combination of techniques. And the indicia 118 can represent any suitable information regarding the sizer, e.g., dimensions, etc. In one or more embodiments, the indicia 118 can indicate the heart valve of which the sizer 100 is representative.

As described herein, the tips 140 can be disposed on posts 130 of the sizer body 110 such that the tips extend from the post receiving surface 134. The post receiving surface 134 can take any suitable shape or combination of shapes. In one or more embodiments, the tips 140 can instead be disposed on the sizer body 110 such that they extend over the interior surface 114 of the sizer body 110.

Figure 6:
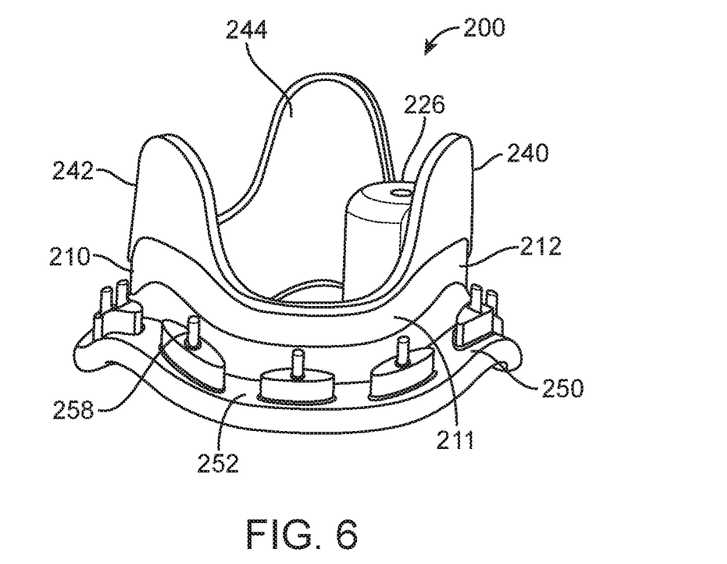
FIG. 6 is a schematic perspective view of another embodiment of a prosthetic valve sizer.
Figure 7:
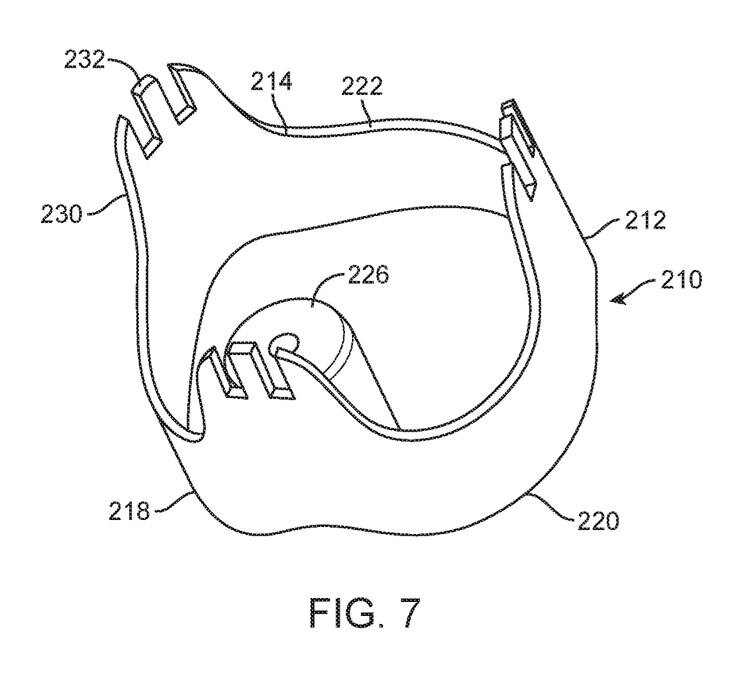
FIG. 7 is a schematic perspective view of a sizer body of the prosthetic valve sizer of FIG. 6.

For example, FIGS. 6-7 are various views of another embodiment of a valve sizer 200. All of the design considerations and possibilities regarding the valve sizer 100 of FIGS. 3-5 apply equally to the valve sizer 200 of FIGS. 6-7. The valve sizer 200 includes a sizer body 210 that includes an annular base 220 and posts 230 extending from the annular base. The sizer 200 also includes tips 240 that extend from one or more posts 230 of the sizer body 210. In one or more embodiments, sizer 200 includes a ring 250 that extends from the sizer body 210 adjacent the annular base 220 of the sizer body.

One difference between valve sizer 200 and valve sizer 100 is that the tips 240 and the ring 250 are integral as can be seen in FIG. 6. The tips 240 and the ring 250 form part of a sizer body covering 242. The covering 242 includes connecting portion 244 that connects the tips 240 to the ring 250.

Another difference between sizers 200 and 100 is that the ring 250 of sizer 200 includes one or more protrusions 258 extending from an outer surface 252 of the resilient ring 250. The protrusions 258 are configured to represent one or more sutures that are used to attach a prosthetic heart valve to tissue of the patient. The protrusions 258 can take any suitable shape or combination of shapes. In one or more embodiments, the protrusions 258 are shaped such that they represent the size and configuration of knots made by a surgeon in sutures used to attach a prosthetic heart valve to the patient's tissue. In one or more embodiments, the protrusions 258 thus allow a surgeon to ascertain the amount of space that sutures will occupy when the heart valve is attached to tissue. The protrusions 258 can be formed using any suitable technique or combination of techniques. In one or more embodiments, the protrusions 258 are integral with the ring 250.

As illustrated in FIG. 7, sizer body 210 includes one or more tabs 232 that extend from posts 230. The tabs 232 can take any suitable shape or combination of shapes. In general, the tabs 232 can be utilized to provide additional surface area for the posts 240 of the valve covering 242 to be attached or molded to the sizer body 210.

Sizer body covering 242 can be disposed on the sizer body 210 using any suitable technique or combination of techniques. In one or more embodiments, the sizer body covering 242 can be molded to the sizer body 210 using any suitable molding technique, e.g., insert molding, injection molding, etc. In one or more embodiments, the sizer body covering 242 can be formed over the sizer body 212 by inserting the sizer body into the sizer body covering 242 and attaching the sizer body covering to the sizer body.

Sizer body covering 242 can be molded over any suitable portion or portions of the sizer body 210. As illustrated in FIG. 6, at least a portion 211 of the sizer body 210 can remain exposed and uncovered by the sizer covering 242. In one or more embodiments, the sizer body covering 242 can cover substantially all of the exterior surface 212 of the sizer body 210. In embodiments where one or more portions 211 of the sizer body 210 remain exposed, the sizer body can include one or more recesses or receiving surfaces that are adapted to receive a portion or portions of the sizer covering 242 such that the covering is flush with the outer surface 212 of the sizer body.

Figure 8:
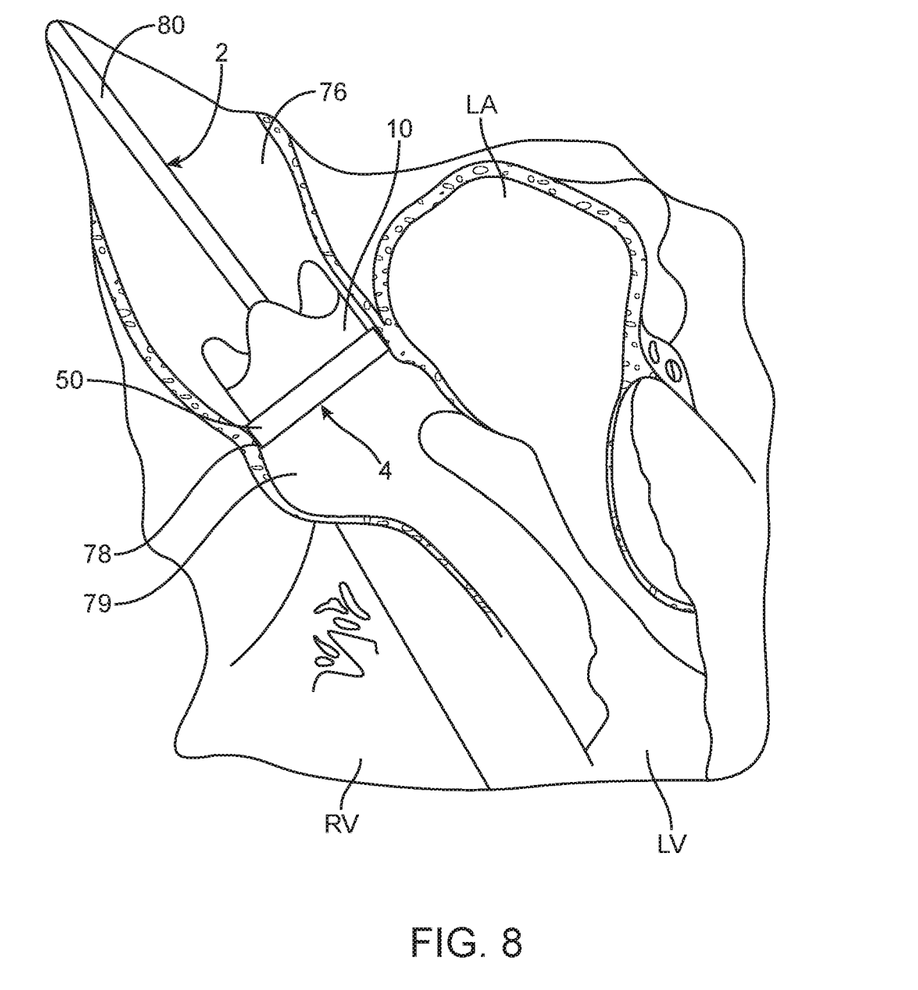
FIG. 8 is a schematic cross-section view of the prosthetic valve sizer assembly of FIG. 1 inserted inside a valve annulus of a patient's heart.

The valve sizers described herein can be utilized with any suitable technique. For example, FIG. 8 is a schematic cross-section view of the sizer assembly 2 of FIG. 1 being utilized inside a patient. During heart valve replacement surgery, the surgeon will have a plurality of sizer assemblies 2 or at least a plurality of sizers 10 at his disposal. Each of the sizer assemblies 2, or more particularly each sizer body 10, corresponds with a different size or version of prosthetic heart valve (e.g., heart valve 60 of FIG. 2), i.e., is representative of or approximates the size, shape, and variable flexibility of an available prosthetic heart valve. The surgeon selects one of the plurality of sizer assemblies 2 or sizers 10 by grasping the grip portion 86 of the handle 80 and inserting a distal end 4 of the sizer assembly into an aortic root 76 of a patient's heart valve annulus 78 as illustrated in FIG. 8.

The surgeon maneuvers the sizer assembly 2 to position the sizer 10 above or within (dependent upon the implant technique being utilized) the heart valve annulus 78 to evaluate the fit of the selected sizer. Since the sizer 10 has a size, shape, and variable flexibility representative of the corresponding prosthetic heart valve 60, the sizer fits within and conforms to the structures within the aortic root 76 in a manner substantially similar to or substantially predictive of how the corresponding prosthetic heart valve would fit within and conform to the structures within the aortic root. With this in mind, the surgeon compares the conformity of the ring 50 to the heart valve annulus 78 and evaluates the feasibility of subsequent suturing of the corresponding prosthetic heart valve 60 (illustrated in FIG. 2) to the heart valve annulus. Furthermore, the surgeon observes and evaluates the positioning of the sizer 10 within the aortic root 76 to ensure there is adequate space for the prosthetic valve and that the positioning of the prosthetic valve will not cause unintentional blockage. In one or more embodiments, the surgeon also evaluates the deflection of the sizer 10 to determine if there is sufficient space between the sizer and the annulus 78 for accessing the ring 50 for suturing. In one or more embodiments where the sizer flexibility matches the flexibility of the prosthetic valve, the clinician can use the sizer to predict whether the fit of the prosthetic valve is too tight, which can cause distortion and/or deformation of the prosthetic valve, thereby potentially leading to sub-optimal performance of the prosthetic valve.

If the surgeon determines that the selected sizer assembly 2, or more particularly the selected sizer 10, is a satisfactory and appropriate fit to the particular patient's heart valve annulus 78, he removes the sizer assembly and selects the size and type of prosthetic heart valve 60 that corresponds with the sizer for subsequent implantation. However, if the surgeon determines that the size or type of the sizer is inappropriate for implantation to a patient's annulus 78, the sizer assembly 2 is removed and a different sized sizer or sizer assembly is selected.

The newly selected sizer assembly 2 is inserted into the aortic root 76 of the patient and evaluated in a similar manner as described herein with respect to the initially selected sizer assembly. This process is repeated until the performing surgeon determines the sizer 10 of a selected sizer assembly 2 to be representative of the appropriate prosthetic heart valve 60. At such a time, the sizer assembly 2 is removed, and a prosthetic heart valve 60, which corresponds to the sizer 10 determined to be appropriate by the surgeon, is selected. Notably, although described and illustrated for use with an aortic valve, a heart valve sizer can be used during heart valve replacement of any of the valves (i.e., mitral valve, tricuspid valve, aortic valve, and pulmonary valve).

In one or more embodiments, not only is the size and flexibility of the sizer 10 analyzed within the aortic root 76 of the patient, but the implantation technique is also evaluated. In particular, a surgeon uses a selected sizer 10 and evaluates the sizer in both a supra-annular and an intra-annular position. This evaluation allows the surgeon to observe whether a particular size of the sizer 10 is more aptly suited for implantation via the super-annular or intra-annular implantation technique. In particular, the surgeon evaluates the size of the ring 50 and the sizer body 12 with respect to the annulus 78 and an annulus opening 79 as well as the flexible conformity of the ring to the annulus and the sizer body within the aortic root 76 in both positions. Such observation allows the surgeon to determine which implantation technique would more beneficially suit the particular patient undergoing the heart valve replacement surgery.

Figure 9:
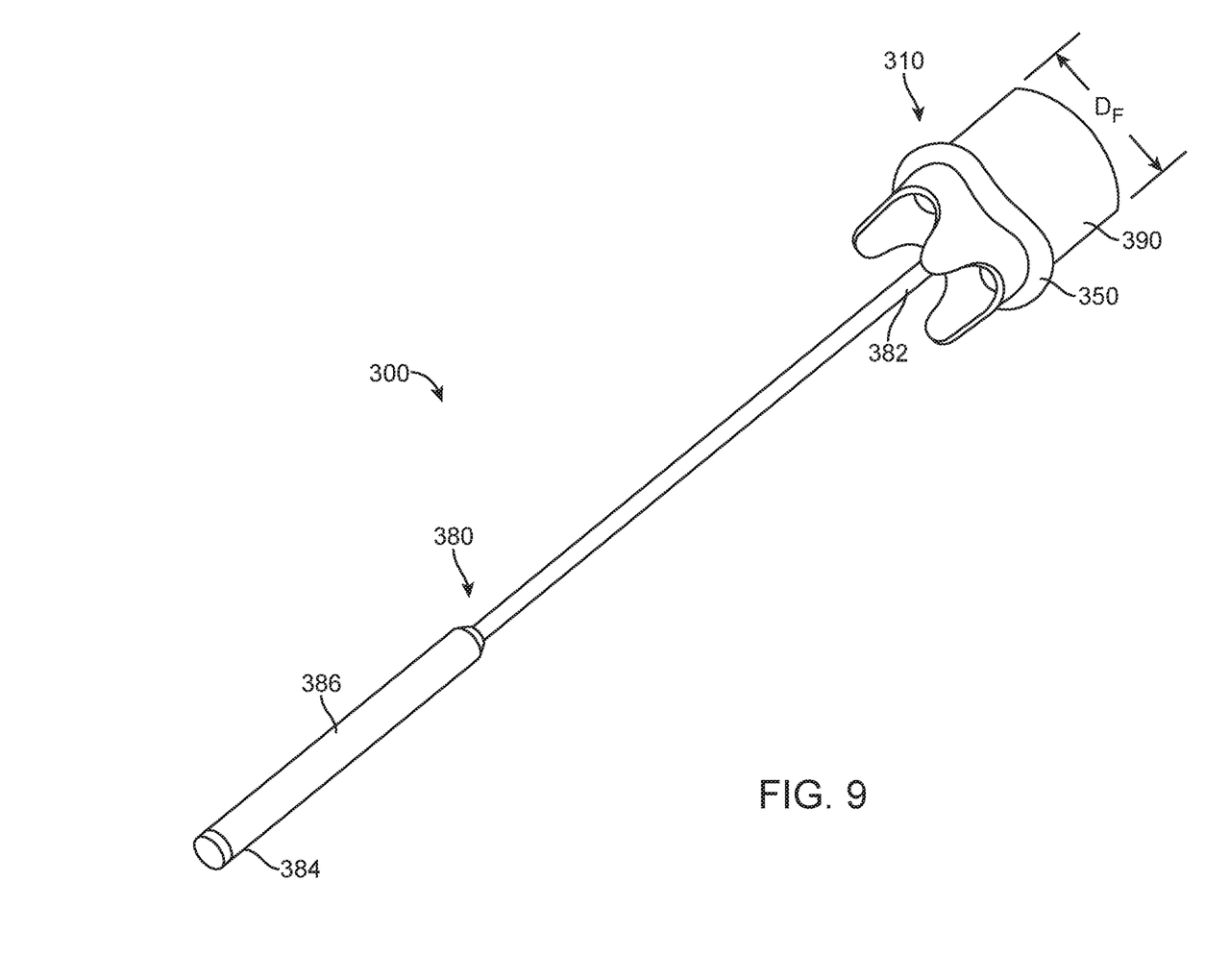
FIG. 9 is a schematic perspective view of another embodiment of a prosthetic valve sizer assembly.

FIG. 9 is a schematic perspective view of another embodiment of a prosthetic heart valve sizer assembly 300. All of the design considerations and possibilities regarding the assembly 2 of FIG. 1 apply equally to the assembly 300 of FIG. 9. The sizer assembly 300 includes a handle 380 and a sizer 310. The handle 380 is similar to the handle 80 described with respect to the sizer assembly 2 of FIG. 1. A first end 382 of the handle 380 is connected to the sizer 310. The sizer 310 can include any sizer, e.g., sizer 100 of FIGS. 3-5. The assembly 300 also includes cylinder sizer 390 that extends from the sizer 310.

The cylinder sizer 390 extends distally from a ring 350 of the sizer 310 in a distal direction. The cylinder sizer 390 can be used to determine the diameter of the valve opening within a patient undergoing heart valve replacement surgery. As such, the particular cylinder sizer 390 placement with respect to the ring 350 is dependent upon the surgical technique being utilized. In particular, for an intra-annular implant technique, the cylinder 390 has a diameter $D_F$ substantially equal to, i.e., within 1 mm of, the outer diameter of ring 350. Conversely, for a supra-annular implant technique, the cylinder sizer 390 has a diameter $D_F$ more nearly representative of the sizer body diameter $D_4$ (FIG. 3). The combination of a cylinder sizer 390 with the sizer 350 allows a surgeon to utilize a number of sizing techniques along with the sizing techniques of the present disclosure.

Figure 10:
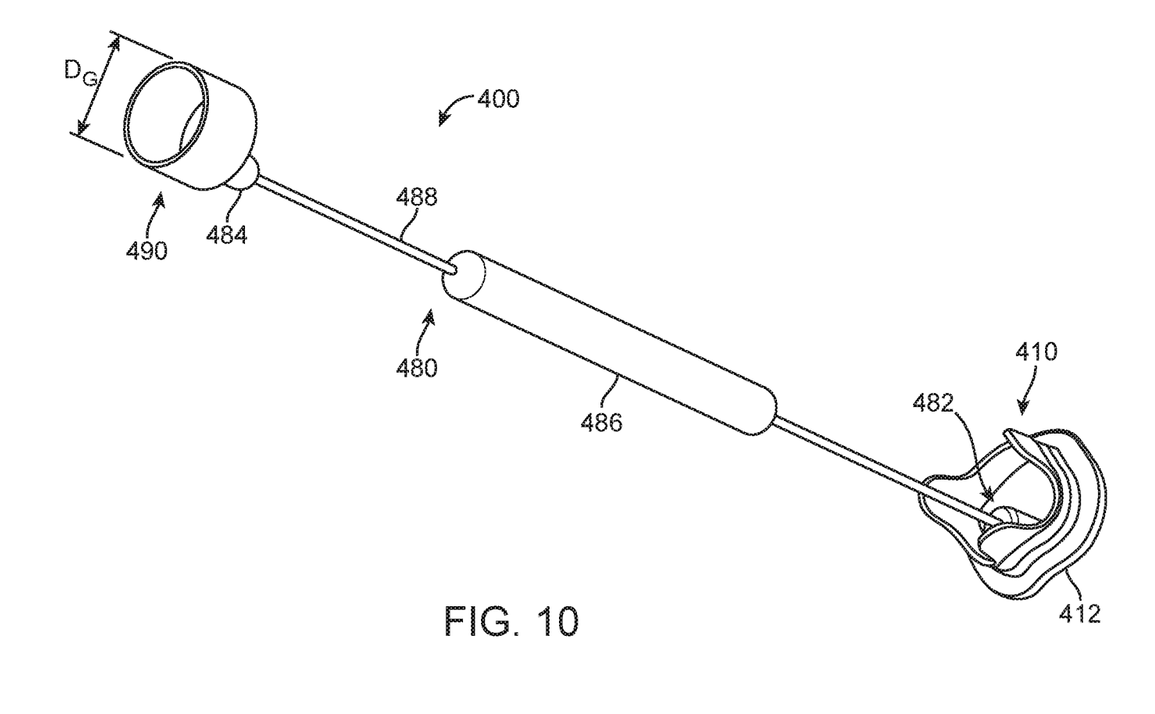
FIG. 10 is a schematic perspective view of another embodiment of a prosthetic valve sizer assembly.

Another alternative embodiment of a prosthetic heart valve sizer assembly 400 is generally illustrated in FIG. 10. All of the design considerations and possibilities regarding the assembly 2 of FIG. 1 apply equally to the assembly 400 of FIG. 10. The sizer assembly 400 includes a handle 480, a sizer 410, and a cylinder sizer 490. The sizer 410 can include any sizer, e.g., sizer 100 of FIGS. 3-5. The handle 480 is similar to the handle 80 (FIG. 1) described herein with respect to the sizer assembly 2 except for those features specifically described herein. The handle 480 defines a first end 482 and a second end 484. The first end 482 is coupled with the sizer 410 in a similar manner as described with respect to the handle 80. The traditional cylinder sizer 490 is coupled with the second end 484 of the handle 480. The cylinder sizer 490 is coupled with the handle 480 via a snap connection, a threaded connection, or any other spatially feasible and biocompatible method of attachment. The cylinder sizer 490 defines a diameter $D_G$ used to size the valve opening (illustrated in FIG. 8) in the patient undergoing prosthetic heart valve replacement. As such, for an intra-annular implant technique, the diameter $D_G$ of the cylinder 490 is substantially equal to the outer ring diameter of a sizer body 412 of sizer 410. Similarly, a sizer assembly 400 used for a supra-annular implant technique includes the cylinder sizer 490 in which the diameter $D_G$ is substantially equal to, i.e., within 1 mm of, the diameter of the sizer body 412 of the sizer 410.

The sizer assembly 400 can be placed within the aortic root 76 (FIG. 8) of a patient with the cylinder sizer 490 as the leading (or distal) end. The cylinder sizer 490 is used by the surgeon to measure the diameter of the heart valve annulus opening. During surgery, the surgeon typically has a number of sizes of the sizer assembly 400 available. The surgeon systemically inserts the differently sized sizer assembly 400 until the cylinder sizer 490 of the currently inserted or selected sizer assembly corresponds with the size of the particular patient's heart valve opening.

Upon determining the proper size of the heart valve opening, the surgeon removes the sizer assembly 400 from the aortic root 76 and subsequently replaces the sizer assembly into the aortic root with the sizer 410 as the leading (or distal) end. Upon insertion of the sizer assembly 400, in particular the sizer 410, the surgeon further evaluates the fit of the sizer 410 including the size and flexibility of the resilient ring and the sizer. Once again it is noted that since the sizer body 410 has a size, shape, and variable flexibility representative of the corresponding prosthetic heart valve 60, the sizer fits within and conforms to the structures within the aortic root 76 in a manner substantially similar to or substantially predictive of how the corresponding prosthetic heart valve 60 would fit within and conform to the structures within the aortic root 76. Therefore, upon determination that the sizer 410 is an appropriate fit to the patient's annulus opening 79, the surgeon selects a prosthetic heart valve 60 corresponding to the sizer assembly 400 for implantation.

If the surgeon determines that the sizer 410 inserted into the patient is inadequate for size or flexibility reasons, he removes the sizer assembly 110 and replaces it with a second sizer assembly having a slightly different sized sizer and repeats the process until a sizer assembly is found with a sizer body that most nearly corresponds to the patient's heart valve annulus. Upon selection of a sizer 410 that most nearly corresponds to the patient's heart valve annulus 78, the sizer assembly 400 is removed and a prosthetic heart valve 60 is selected that corresponds to the selected sizer assembly.

In general, the heart valve sizer in accordance with the present disclosure includes a body with a shape, a size, and a variable flexibility representative of or substantially similar to an available heart valve prosthesis, such as a prosthetic heart valve. These characteristics of the sizer allows a surgeon to not only evaluate the size of an annulus opening but also to evaluate the overall fit and conformity of a particular prosthesis to an annulus and/or within a patient's annulus opening. The evaluation of the representative body within the aortic root provides the surgeon with additional knowledge, thereby, allowing him to select a heart valve prosthesis and/or technique of implantation that is more likely to fit and more suitable to the heart annulus of the particular patient. The added certainty concerning the size of the prosthesis and method of implantation not only prevents waste of discarded prostheses but also saves time during the heart valve replacement surgery, thereby benefiting the overall prognosis of the patient. Further, tips provided on one or more posts of the prosthetic valve sizer that, in one or more embodiments, or more flexible than a body of the sizer, can prevent damage to tissue as the surgeon inserts and removes the sizer.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A prosthetic valve sizer comprising:
   a sizer body comprising an annular base and at least two posts extending from the annular base; and
   a resilient tip extending from each of the at least two posts of the sizer body, the resilient tip comprising a material different from and more flexible than a material of the sizer body.

2. The valve sizer of claim 1, further comprising a resilient ring extending from the sizer body adjacent the annular base of the sizer body.

3. The valve sizer of claim 2, wherein the material of the resilient tip is the same as a material of the resilient ring.

4. The valve sizer of claim 1, wherein the sizer body is resilient.

5. The valve sizer of claim 1, wherein the valve sizer is sized and shaped to replicate the size and shape of a prosthetic valve.

6. The valve sizer of claim 1, wherein each of the at least two posts of the sizer body comprises a tab, wherein the tab is disposed within the resilient tip.

7. The valve sizer of claim 1, wherein the sizer body further comprises a receiver configured to receive a first end of a handle.

8. The valve sizer of claim 1, wherein the valve sizer is sterilizable for reuse.

9. A valve sizer assembly comprising:
   a handle comprising a first end and a second end;
   a prosthetic valve sizer connected to the first end of the handle, the prosthetic valve sizer comprising:
      a sizer body comprising an annular base and at least two posts extending from the base; and
      a resilient tip extending from each of the at least two posts of the sizer body, the resilient tip comprising a material different from and more flexible than a material of the sizer body.

10. The assembly of claim 9, wherein the prosthetic valve sizer further comprises a resilient ring extending from the sizer body adjacent the annular base of the sizer body.

11. The assembly of claim 9, wherein the sizer body of the prosthetic valve sizer comprises a receiver adapted to selectively receive the first end of the handle.

* * * * *